(12) United States Patent
Msika et al.

(10) Patent No.: US 8,642,553 B2
(45) Date of Patent: Feb. 4, 2014

(54) ACACIA MACROSTACHYA SEED EXTRACT AND COMPOSITIONS CONTAINING SAME

(75) Inventors: Philippe Msika, Versailles (FR); Alex Saunois, Nogent-le-Roi (FR); Sophie Leclere-Bienfait, Dreux (FR); Caroline Baudoin, Rambouillet (FR)

(73) Assignee: Laboratoires Expanscience, Courbevoie (FR)

( * ) Notice: Subject to any disclaimer, the term of this patent is extended or adjusted under 35 U.S.C. 154(b) by 0 days.

(21) Appl. No.: 13/512,578

(22) PCT Filed: Nov. 30, 2010

(86) PCT No.: PCT/EP2010/068574
§ 371 (c)(1),
(2), (4) Date: May 29, 2012

(87) PCT Pub. No.: WO2011/064402
PCT Pub. Date: Jun. 3, 2011

(65) Prior Publication Data
US 2012/0238506 A1    Sep. 20, 2012

(30) Foreign Application Priority Data

Nov. 30, 2009  (FR) ..................... 09 58525

(51) Int. Cl.
| | | |
|---|---|---|
| A61K 38/02 | (2006.01) | |
| A61K 8/64  | (2006.01) | |
| A61P 17/00 | (2006.01) | |
| A61Q 19/00 | (2006.01) | |
| A61P 7/00  | (2006.01) | |
| A61P 3/00  | (2006.01) | |
| C12P 21/06 | (2006.01) | |

(52) U.S. Cl.
USPC .................... 514/18.8; 514/18.6; 514/1.1

(58) Field of Classification Search
None
See application file for complete search history.

(56) References Cited

FOREIGN PATENT DOCUMENTS

| DE | 10 2006 005 767 | | 8/2007 | |
|----|-----------------|---|--------|---|
| FR | 2 778 565       |   | 11/1999 | |
| FR | 2 902 335       |   | 12/2007 | |
| JP | 2002322076 A    | * | 8/2002 | A61K 35/78 |
| WO | WO 2004/089392 A1 | | 10/2004 | |
| WO | WO 2005/105123 A1 | | 11/2005 | |
| WO | WO 2005/115421 A1 | | 12/2005 | |

OTHER PUBLICATIONS

Houerou, L. *Acacia macrostrachya* Reichenb. ex. Benth. FAO. http://www.fao.org/ag/AGP/AGPC/doc/Gbase/DATA/pf000358.htm:2003.*
Bassett S. Anatomy and Physiology. 2005.*
Brain P. South African Journal of Science. 83;422-427:1987.*
Seydou O. Utilisation des graines de *Acacia macrostachya* Rchend. ex DC. comme source de proteines dans l'aimentation des poulets de chair. Univ Polytech de Bobo-Dioulasso. 2008.*
Aly et al. J App Sci Res. 7(7);1057-1062:2011.*
Adewusi et al., "Chemical composition of *Acacia colei* and *Acacia tumida* seeds—potential food sources in the semi-arid tropics," Food Chemistry, vol. 80, pp. 187-195, 2003.
Sere et al., "Etude d'une plante de la pharmacopee traditionnelle: *Acacia macrostachya*," Medecine d'Afrique Noire, vol. 30, No. 1, pp. 29-34, 1983.
Mustafa et al., "Antimicrobial Activity of *Acacia nilotica* subspp. *nilotica* Fruit Extracts," Pharm. Pharmacol. Commun., vol. 5, pp. 583-586, 1999.
Brain, "Immunology and phylogeny: a preliminary study of *Acacia*," South African Journal of Science, vol. 83, pp. 422-427, Jul. 1987.
Anonymous, "*Acacia macrostachya* auct.," African Plant Database, http://www.ville-ge.ch/musinfor/bd/cjb/africa/details.php?langue=an&id=76770, Jan. 1, 2009, retrieved Jul. 1, 2010.
International Search Report issued in application No. PCT/EP2010/068574 on Oct. 27, 2011.
M. Ouetian Bognounou, Director of Floristic and Ethnobotany Research, "Expert Report Part 1: Inventory and traceability of local traditional skills; *Acacia macrostachya* Reichenbach. Ex DC (Mimosaceae)," INERA/CNRST—Ouagadougou—Burkina Faso, Nov. 2010, 13 pages including English abstract.
Tapsoba et al, "Use of medicinal plants for the treatment of oral diseases in Burkina Faso," Journal of Ethno-Pharmacology, vol. 104, 2006, pp. 68-78.

* cited by examiner

*Primary Examiner* — Karlheinz R Skowronek
*Assistant Examiner* — Schuyler Milton
(74) *Attorney, Agent, or Firm* — Foley & Lardner LLP

(57) ABSTRACT

The invention relates to a composition containing an extract of seeds of *Acacia macrostachya*. Advantageously the composition is cosmetic, pharmaceutical, dermatological or nutraceutical. The invention also relates to a method for extracting a *Acacia macrostachya* seed extract, as well as to the resulting extract. The invention further relates to one such composition or one such extract for use in the prevention or treatment of disorders and diseases affecting the skin, mucosae or appendages, for use in the prevention or treatment of vascular disorders and for use in the prevention or treatment of adipose tissue alterations. Moreover, the invention relates to a method for cosmetic care of the Skin, appendages and mucosae in order to improve the condition or appearance thereof, comprising the administration of one such composition or one such extract.

33 Claims, No Drawings

ACACIA MACROSTACHYA SEED EXTRACT AND COMPOSITIONS CONTAINING SAME

The invention relates to a composition containing an extract of seeds of *Acacia macrostachya*, such as a peptide and oside extract of *Acacia macrostachya* seeds. The composition is advantageously cosmetic, pharmaceutical, dermatological, or nutraceutical. The invention also relates to a method for extracting an *Acacia macrostachya* seed extract, as well as the extract obtainable by said method. The invention also relates to one such composition or one such extract for its use in the prevention or the treatment of disorders or diseases affecting the skin, the mucosae or the appendages, for its use in the prevention or the treatment of vascular disorders, or instead for its use in the prevention or the treatment of alterations of the adipose tissue. The invention finally relates to a method of cosmetic care of the skin, the appendages or the mucosae, in order to improve the condition or appearance thereof, comprising the administration or consisting in administering one such composition or one such extract.

The genus *Acacia* comprises a large number of ligneous species well adapted to hot and dry climates, with very low precipitation. Certain species are widespread in the semi-desertic tropical regions of West Africa, Australia, Pakistan, etc. Many *Acacia* thus have an ecological role and some an important economic role: *A. Senegal*, source of gum Arabic; *A. catechu*, source of tannins; *A. dealbata*, (our mimosa) horticultural with ornamental flowers. In comparison with these species well known in the West, *Acacia macrostachya* has remained quite marginal. It is above all the alimentary use of the seeds thereof that has led to some written works regarding it. Current data concerning it mainly stems from two or three Western works on African Sahelian plants, and documents of international organisations written by authors who are for the most part from Burkina Faso. For instance, this traditional use is perfectly set out in the reports of Mr. Ouétian Bognounou, Officier and Chevalier de l'Ordre National, Chevalier des Palmes Académiques, floristics and ethnobotanics research officer of the INERA of Burkina Faso, co-authored with Mr. Marc Olivier, ethnobotanics consultant.

*Acacia macrostachya* is a plant very little known outside of the savannah and urban areas of West Africa, as well as here and there in other dry regions where it forms part of the landscape and where the seed is consumed. No part of this plant is the subject of any significant trade between countries. The media and commercial firms of Western countries have not communicated until now on *Acacia macrostachya*.

The Plant *Acacia macrostachya*

This shrub, the botanical name of which is *Acacia macrostachya* Rchb. Ex DC., belongs to the order of Fabales and to the botanical family of Mimosaceae. The common names for the plant in Burkina Faso are: zanmné, karitiga, zamenega, kiese mamonguala (the tree that catches in passing); in Senegal, 16 different names from 12 ethnic groups.

This sarmentous and thorny shrub of 2 to 5 meters height can occasionally become a tree reaching 8 m, with a narrow and open crown. Its bark is often cracked, fibrous, grey with white streaks. It has brown pubescent branches, provided along the length thereof with dispersed and hooked thin thorns of one cm length. The stalks are long and flexible.

Its soft green alternate two-edge leaves are all laid out in the same plane. They include a petiole of 8 to 22 cm length, pubescent and thorny underneath, bearing a lengthened round gland before the first pair of pinnules. Each petiole has 20 to 30 pairs of pinnules (petiolule) with 20 to 50 pairs of foliolules per pinnule.

The foliolules are short, pubescent, linear to symmetrical.

The thorny inflorescence is formed of 1 to 2 cylindrical spikes, from 7 to 8 (5-12) cm long, with numerous flowers arranged at the axile of the leaves, of cream towards yellowing colour. Bees gather nectar and pollen from the flowers. *Acacia* has a high melliferous value. Flowering takes place at the end of the dry season or at the start of the rainy season after foliation.

The fruit is a thin flattened and slightly wavy, oblong pod (7 to 15×1.5 to 2.0 cm), acuminate at the two ends, red brown at maturity. It contains 7 to 8 seeds (2-3 seeds according to A. Sere et al., 1983). The latter are brown, round and flattened. They measure 7 to 8 mm diameter. The weight of the seeds is approximately 77 g for 1000 seeds.

Seed Characteristics

Literature data relative to the chemical composition of *Acacia macrostachya* seeds are almost inexistent.

The seeds could be, it appears, very rich in proteins, iron and vitamins C. A summary article written in French (Parkouda et al, 2006) relates to the evaluation of the nutritional quality (carbohydrates, lipids, proteins and minerals) of fruit species of Burkina Faso including *Acacia macrostachya*, but do not detail the contents thereof.

Nutritional analyses carried out by the Applicant on seeds of different origin show that they can contain for example:

38% of fibres
38% of proteins
8% of lipids
2.5% of saccharose

PRIOR ART

Medicinal Use:

*Acacia macrostachya* is mentioned as being a medicinal plant in Guinea and in Senegal (Penso, 2001), as well as in Mali (Boullard, 2001). However, the seed seems to be very little used for therapeutic purposes.

Zaméné (the washed and cooked boiled seed) reputedly cures stomach pains and is appreciated by persons suffering from arterial hypertension.

Complementary Observations:

In popular Sahelian medicine, especially in Senegal, the bark (Arbonnier, 2002; Neuwinger, 1996) or the boiled young leaves (Neuwinger, 1996) are used in gastro-intestinal disorders in the event of flatulence, vomiting and diarrhoea. The bark is also employed as a disinfectant and anthelmintic (Arbonnier, 2002; Neuwinger, 1996). The roots are prescribed in cases of blennorrhagia and syphilis (Arbonnier, 2002).

In Gambia, the macerated roots are employed for stomach disorders (Neuwinger, 1996). The leaves, used externally or internally, reputedly constitute an antidote to snake venom (Arbonnier, 2002).

In Mali, barks, roots and leaves are advocated to calm stomach pains in children, dysenteries and diarrhoeas (Boullard, 2001).

In Casamance, in Mali and in Burkina Faso, the root is advocated by tradi-practitioners for aphrodisiac purposes (Sere et al, 1983).

In Burkina Faso, the decoction of the leaves is applied locally to treat dental abscesses (Tapsoba and Deschamps, 2006).

Dermatological and Cosmetic Uses:

No current use has been reported to date.

DESCRIPTION OF THE INVENTION

The Applicant has discovered that the extracts of seeds of *Acacia macrostachya* have cosmetic and dermatological properties never recorded until now. In particular, it is the first time that *Acacia macrostachya* extracts are used as such, for the specific properties thereof.

The invention relates to a composition containing an extract of seeds of *Acacia macrostachya*, said seed extract containing peptides and/or sugars, advantageously a mixture of peptides and sugars, optionally in association with an appropriate excipient.

The composition is advantageously cosmetic, pharmaceutical, dermatological or nutraceutical. Said composition is preferably formulated to be administered by external topical or oral route.

Preferentially, the *Acacia macrostachya* seed extract is a peptide and oside extract.

"Peptide and oside extract" is taken to mean an extract containing a majority of, or essentially, peptides and monosaccharides (sugars).

Advantageously, the *Acacia macrostachya* seed extract is essentially constituted of a mixture of peptides and sugars.

In a particularly advantageously manner according to the invention, the *Acacia macrostachya* seed extract is substantially cleared of any residual native protein, because said proteins can cause allergic reactions that it is wished to avoid.

Typically, the *Acacia macrostachya* seed extract is substantially cleared of free amino acids.

The extract according to the present invention advantageously comprises 10 to 90% by weight of peptides and 10 to 90% by weight of total sugars, the percentages being expressed in relation to the total weight of said extract.

In a particular embodiment of the present invention, the extract comprises 20 to 70%, advantageously 20 to 60%, advantageously 30 to 65%, typically 30 to 55%, in particular 45 to 50%, by weight of peptides In another particular embodiment of the present invention, the extract comprises 20 to 60%, advantageously 30 to 55%, in particular 45 to 50%, by weight of sugars.

According to a preferred aspect of the invention, the peptide and oside extract comprises 50% by weight of peptides and 45% by weight of sugars, the percentages being expressed in relation to the total weight of active material of said extract before adding for example an optional drying support.

According to a particular characteristic of the present invention, the peptides/sugars ratio of the extract is greater than 0.75, and advantageously comprised between 1 and 2.

According to an advantageous variant of the invention, the composition contains 0.001 to 10%, typically 0.01 to 5%, by weight of extract, expressed in percentage of dry extract.

The invention also relates to a method for preparing a peptide and oside extract of *Acacia macrostachya* seeds.

Advantageously according to the invention, the method for preparing a peptide and oside extract of *Acacia macrostachya* seeds comprises the following successive steps:
grinding of *Acacia macrostachya* seeds,
dispersion of the ground *Acacia macrostachya* seeds in water or in aqueous phase, advantageously at a pH comprised between 3.0 and 9.0 and at a temperature comprised between 20 and 90° C.,
hydrolysis, advantageously enzymatic, of said dispersion, and
recovery of the peptide and oside extract.

Before being dispersed, the ground seeds may be delipidated, especially in ethanol.

In a particularly advantageous manner according to the invention, following the dispersion in aqueous phase, a hydrolysis of said dispersion is carried out, such as an enzymatic and/or chemical hydrolysis, and quite particularly advantageously an enzymatic hydrolysis.

Typically, the enzymatic hydrolysis is carried out by one or more suitable enzymes in optimal conditions of pH and temperature, known to those skilled in the art, for example at a pH comprised between 3.0 and 9.0 and typically at a temperature comprised between 20 and 90° C., advantageously by at least one carbohydrase such as a pectinase or cellulase, or by a mixture of proteases and carbohydrases, such as pectinases, cellulases, arabanases, hemicellulases, xylanases and β-glucanases, then the peptide and oside extract is recovered.

According to an advantageous aspect of the invention, the hydrolysis is an enzymatic hydrolysis by at least one protease or a carbohydrase.

The enzymatic hydrolysis of the dispersion may be followed if necessary by a heat treatment in order to denature the enzymes, typically between 80 and 100° C.

The hydrolysis step of the method according to the invention is very important, since it makes it possible to transform or "cut up" the native proteins present in the *Acacia* seeds into peptides. This step also advantageously makes it possible to transform or to "cut up" the polysaccharides present in the *Acacia* seeds into oligosaccharides or monosaccharides.

In a particularly advantageous manner according to the invention, the method comprises a hydrolysis step such as an enzymatic hydrolysis, then a step of ultra filtration for example at a cut off point comprised between 10000 Daltons and 15000 Daltons, to eliminate residual proteins that are potentially allergenic and optionally enzymes.

In a particular embodiment according to the invention, the method also comprises a step of nano-filtration with for example a cut-off point comprised between 100 Daltons and 300 Daltons, advantageously between 130 and 300 Daltons, typically between 200 Daltons and 300 Daltons, to eliminate free amino acids or mineral salts, following the ultra-filtration step.

According to an advantageous variant of the invention, following the hydrolysis of the dispersion and prior to the recovery of the peptide and oside extract, a filtration or a centrifugation is carried out, optionally followed by an ultra-filtration, diafiltration, and/or nanofiltration.

Preferentially, by way of example, the peptide and oside extract may be obtained according to the following method:
a) delipidation of the seeds ground beforehand by dispersion at 10% of dry matter in 96% ethanol;
b) after elimination of the ethanol, replacing in solution the seeds thereby delipidated at 10% of dry matter in water;
c) enzymatic hydrolysis of the carbohydrates by combined action of a pectinase/cellulase (Peclyve LI from the Lyven Company for example) and another mixture of carbohydrates with complementary activities, such as arabanase, β glucanase, hemicellulase, xylanase (Viscozyme L from the Novozymes company for example) in optimal conditions of pH and temperature for the activity of these enzymes;
d) followed by a hydrolysis by an alkaline protease (for example Prolyve 1000 from the Lyven company);
e) heat treatment in order to denature the enzymes;
f) centrifugation, ultrafiltration and/or diafiltration on kDa membranes in order to eliminate potentially allergenic residual proteins;
g) nanofiltration on 200 Da membrane in order to eliminate mineral salts or free amino acids for example.

Advantageously according to the invention, following the recovery of the peptide and oside extract, at least one of the following steps is carried out:
- decoloration of the extract thereby obtained, for example in the presence of activated carbon or by any other means known to those skilled in the art, and
- drying of the extract obtained on a support or without support.

Advantageously, the peptide and oside extract may be dried by methods known to those skilled in the art, in the presence or not of, for example, maltodextrins or fibres of *Acacia* type (Fibregum®, CNI Company); typically according to a ratio which can vary from 0% to 80% of support in relation to the percentage of dry matter obtained in the liquid form of the extract and preferentially dried by lyophilisation in order to obtain in the final powder 50% of dry matter stemming from the extract and 50% of lyophilisation support.

Example of Liquid Peptide and Oside Extract Thereby Obtained

1—Physical-Chemical Analysis (%/Total Dry Matter)
Dry extract (2 h, 105° C., ventilated oven): 6.5%
pH: 4
α-amino nitrogen (OPA, leucine equivalent): 24%
Peptides (Kjeldahl, N×6.25): 47%
Soluble sugars (HPLC): 45% of which typically glucose, fructose and saccharose
Total ash: 16%
Polyphenols (Folin-Cioccalteu, in gallic acid): 3%
The extract according to the invention thus typically contains polyphenols.
2—Breakdown Profile of the Molar Masses of Soluble Peptides

| | |
|---|---|
| Less than 130 Da | 20% |
| Between 130-300 Da | 17% |
| Between 300-1200 Da | 48% |
| Between 1200-3500 Da | 14% |
| Greater than 3500 Da | ≤1% |

The present invention also relates to an *Acacia macrostachya* seed extract obtainable by the aforementioned method. One such extract contains advantageously 10 to 90% by weight of peptides and 10 to 90% by weight of sugars.

In a particular embodiment of the present invention, the extract comprises 20 to 70%, advantageously 20 to 60%, advantageously 30 to 65%, typically 30 to 55%, in particular 45 to 50%, by weight of peptides In another particular embodiment of the present invention, the extract comprises 20 to 60%, advantageously 30 to 55%, in particular 45 to 50%, by weight of sugars.

Typically, the extract according to the present comprises monosaccharides or oligosaccharides, such as glucose, fructose, saccharose, or mixtures thereof. In particular, sugars of the extract are compounds mainly of glucose, fructose and saccharose.

According to a particular characteristic, the peptides/sugars ratio of the extract according to the invention is greater than or equal to 0.75, and advantageously comprised between 1 and 2.

Advantageously according to the invention, the peptides of the extract have a molecular weight less than or equal to 3500 Daltons. In particular, the peptides of the extract have mainly a molecular mass less than or equal to 1200 Daltons, typically between 300 and 1200 Daltons.

Typically, the peptide and oside extract according to the invention substantially does not contain residual proteins that are potentially allergenic.

In a particular embodiment, the peptide and oside extract according to the invention substantially does not contain free amino acids.

According to another aspect of the invention, the composition may moreover comprise at least one other active compound in addition to the *Acacia macrostachya* seed extract.

Said other compound may be selected from all the compounds and their functional equivalents, listed below.

Said other compound may in particular be selected from active ingredients conventionally used in dermatology or cosmetics such as emollients, moisturising active ingredients, keratoregulators, keratolytics, agents for restructuring the cutaneous barrier, PPAR agonists (or Peroxysome Proliferator Activated Receptor), RXR or LXR agonists, vitamin D or corticoid receptor agonists, activators of the differentiation of keratinocytes (retinoids, Calcidone®, calcium), sebo-regulating agents, anti-irritant agents, thickening agents, anti-inflammatory agents, anti-oxidant agents and anti-ageing agents.

Said other compound may also be selected from active ingredients having a complementary therapeutic or cosmetic action, such as antibiotics, pre and probiotics, anti-bacterial agents, the anti-fungal agent compounds, anti-viral agents, preservatives, immunomodulators (tacrolimus or pimecrolimus), oxazolines, growth factors, cicatrising agents or eutrophic molecules, medicines, pigmenting or hypopigmenting agents, lipolytic agents or lipogenesis inhibitors or instead anti-cellulite or slimming agents, mineral or organic sun filters and screens (pigmentary or ultrafine), conventional or functional foodstuffs: hyper or hypoglycaemic agents, anti-fat or anti-cellulite nutrients, anti-cholesterol, anti-oxidant, energisers, reconstituents, or having an impact on the secondary signs of menopause.

Said other compound can also be selected from natural plant extracts (parts of plants extractible in aqueous or oily phase: polyphenols, flavonoids, other peptides and sugars, etc.), compounds containing unsaponifiables of vegetable oils, sterolic unsaponifiables or products that can contain same (unsaponifiables of vegetable oils, especially unsaponifiables of soya oil, unsaponifiables of vegetable butters or buttery materials and mixtures thereof, unsaponifiables of natural waxes, unsaponifiables of oily extracts, unsaponifiables of industrial oily by-products, unsaponifiables of extracts of fatty bodies of animal origin, unsaponifiables of marine oils, unsaponifiables of extracts of lactic fatty matter, unsaponifiables of lipid extracts of unicellular organisms, unsaponifiables of lipid extracts of seaweed and marine organisms, etc), sterols, stanols, phytosterols, phytostanols, tocopherols, concentrates of oils of sunflower, rape and/or palm, trace elements, vitamins, omega 3, 6 or 9 fatty acids, hypoglycemic or hyperglycemic or sweetening plants.

The moisturising/emollient active ingredients the most used are glycerine or derivatives thereof, urea, pyrrolidone carboxylic acid and derivatives thereof, hyaluronic acid of any molecular weight, glycosaminoglycans and any other polysaccharides of marine, plant or biotechnological origin such as for example xanthan gum, Fucogel®, certain fatty acids such as lauric acid, myristic acid, omega 3, 6 and 7, 9 type poly- and mono-unsaturated fatty acids such as linoleic acid and palmitoleic acid, sunflower oleodistillate, the peptides of avocado, Cupuaçu butter. Modulators of epidermal differentiation key proteins of the *stratum corneum* or *granu-*

*losum* that can be used in association are advantageously retinoids, peptides of Lupin, sugars of avocado, or a Quinoa peptide extract.

The most conventional anti-inflammatory/anti-irritant soothing agents are glycyrrhetinic acid (derivatives of liquorice) with salts and esters thereof, lipoic acid, beta-carotene, vitamin B3 (niacinamide, nicotinamide), vitamin E, vitamin C, vitamin B12, flavonoids (green tea, quercetine, etc.), lycopene or lutein, sugars of avocado, the oleodistillate of avocado, arabinogalactane, peptides of Lupin, total extract of Lupin, peptide extract of Quinoa, Cycloceramide® (derivative of oxazoline), isoflavones such as for example genisteine/genistine, daidzeine/daidzine, source or thermal waters (Water of Avene, Water of La Roche Posay, Water of Saint Gervais, Water of Uriage, Water of Gamarde), extracts of Goji (*Lycium barbarum*), peptides or complexes of plant amino acids or instead topical disulone, or steroidal anti-inflammatory drugs (SAID), such as corticoids, or non-steroidal anti-inflammatory drugs (NSAID).

Among the keratoregulator/keratolytic agents the most used are: the acids of alpha hydroxyl acid (AHA) fruits (citric acid, glycolic acid, malic acid, lactic acid, etc.), esters of AHA, associations of AHA with other molecules such as the association malic acid and proteins of almonds (Keratolite®), the association of glycolic acid or lactic acid with arginine or instead the association of hydroxy-acid with lipidic molecules such as LHA® for lipo-hydroxy-acid, complexes of amphoteric hydroxyacids—AHCare, azelaic acid and salts and esters thereof, willow bark (*Salix alba* bark extract), salicylic acid (beta hydroxyl acid—BHA), and derivatives thereof such as capryloyl salicylic acid or in association with other molecules such as the association salicylic acid and polysaccharide, tazarotene, adapalene, as well as molecules of the family of retinoids such as: tretinoin, retinaldehyde, isotretinoin, or retinol.

The sebo-regulating agents that can be used in association are advantageously selected from the group constituted of 5-alpha reductase inhibitors such as for example the active ingredient 5-alpha Avocuta®. Zinc (and the gluconate, salicylate and pyroglutamic acid salts thereof) also exhibits a sebo-suppressor activity. Spironolactone, anti-androgene and aldosterone antagonist, which bring about a significant reduction in the level of sebum secretion, may also be cited. Other molecules such as for example *Cucurbita pepo*, extract of pumpkin seeds, and marrow seed oil, sabal, limit the production of sebum through inhibition of 5α-reductase. Other sebo-regulators of lipidic origin acting on the quality of the sebum, such as linoleic acid, have an interest.

Growth factors that can be used in association are advantageously becaplermine and TGF-beta, EGF, NGF, VEGF.

Antioxidant agent is taken to mean a molecule that reduces or prevents the oxidation of other chemical substances. The antioxidants that can be used in association are advantageously selected from the group constituted of thiols and phenols, by derivatives of liquorice such as glycyrrhetinic acid with salts and esters thereof, alpha bisabolol, the extract of ginkgo biloba, calendula, Cycloceramide® (derivative of oxazoline), the peptides of avocado, trace elements such as copper, zinc, and selenium, lipoic acid, vitamin B12, vitamin B3 (niacinamide, nicotinamide), vitamins C, vitamins E, co-enzyme Q10, krill, glutathione, BHT for butyl hydroxy toluene, BHA for butyl hydroxy anisol, lycopene or lutein, beta-carotene, the large family of polyphenols such as tannins, phenolic acids, anthocyans, flavonoids with for example the extracts of green tea, red fruits, cacao, grapes, *Passiflora incarnata, Citrus* or instead isoflavones such as for example genisteine/genistine, daidzeine/daidzine. In the group of antioxidants are also found anti-glycation substances, such as carnosine or certain peptides, n-acetyl-cysteine, as well as antioxidants or antiradical enzymes such as SOD (super oxide dismutase), catalase, glutathione peroxidase, thioredoxine reductase and agonists thereof.

Agents for cicatrising and restructuring the cutaneous barrier, making it possible to stimulate the synthesis of key lipids of the epidermis, and that can be used in association are advantageously vitamin A, panthenol (vitamin B5), sugars of avocado, Lupeol, peptide extract of Maca, peptide extract of Quinoa, arabinogalactane, zinc oxide, magnesium, silicon, madecassic or Asiatic acid, dextran sulphate, the coenzyme Q10, glucosamine and derivatives thereof, chondroitin sulphate and generally glucosaminoglycans or GAG, dextran sulphate, ceramides, cholesterol, squalane, phospholipids, peptides of soya fermented or not, plant peptides, marine, plant or biotechnological polysaccharides such as seaweed extracts or fern extract, trace elements, the extracts of tannin plants such as the tannins derived from gallic acid known as gallic or instead hydrolysable tannins, initially found in the gall nut, and catechic tannins resulting from the polymerisation of flavanic units, the model of which is supplied by Cachou (*Acacia catechu*). The trace elements that can be used are advantageously selected from the group constituted of copper, magnesium, manganese, chromium, selenium, silicon, zinc and mixtures thereof. Concentrates of sunflower, more advantageously linoleic concentrates of sunflower, such as the active ingredient commercialised by the Laboratoires Expanscience, Soline®, unsaponifiables of vegetable oil, such as Avocadofurane®, or PPAR agonists (rosiglitazone, pioglitazone), RXR, LXR may also be used.

The anti-ageing agents that can act on subjects of advanced age are antioxidant agents and in particular vitamin C, or instead vitamin A, retinol, retinal, hyaluronic acid of any molecular weight, Avocadofurane®, the peptides of Lupin, the peptide extract of Maca.

The antifungal compounds that can be used in association are advantageously econazole and ketoconazole.

The antiseptic preservatives that can be used in association are for example triclosan, chlorhexidine, quaternary ammoniums.

The antibiotics that can be used in association are advantageously fusidic acid, penicillin, tetracyclines, pristinamycin, erythromycin, clindamycin, mupirocine, minocycline, doxycycline. The anti-viral agents that can be used in association are advantageously acyclovir and valacyclovir. The preservatives that can be used in association are for example those generally used in cosmetic or in nutraceutical applications, molecules with anti-bacterial activity (pseudo-preservatives) such as caprylic derivatives such as for example capryloyl glycine and glyceryl caprylate, such as hexanediol, and sodium levulinate, derivatives of zinc and of copper (gluconate and PCA), phytosphingosine and derivatives thereof, benzoyl peroxide, piroctone olamine, zinc pyrithione, selenium sulphide.

The solar protection active ingredients that can be used in association are advantageously UVB and/or UVA sun filters or screens; such as mineral and/or organic screens or filters known to those skilled in the art who will adapt their choice and their concentrations as a function of the requisite degree of protection.

By way of example of solar protection active ingredient may especially be cited titanium dioxide, zinc oxide, methylene bis-benzotriazolyl tetramethylbutylphenol (trade name: TINOSORB M) and Bis-ethylhexyloxyphenol methoxyphenyl triazine (trade name: TINOSORB S), octocrylene, butyl methoxydibenzoylmethane, terephthalylidene dicamphor sulphonic acid, 4-methylbenzylidene of camphor, benzophenone, ethylhexyl methoxycinnamate, ethylhexyl dimethyl PABA, diethylhexyl butamido triazone.

The slimming agents that can be used in association are advantageously caffeine, fucus, plant extracts such as for example: extract of ivy, cacao, guarana, small holly, green tea, yerba-mate, Sichuan pepper, horse chestnut, *Centella asiatica*, carnithine, glauscine, escine, extract of butcher's broom (*Ruscus esculentus*), isoflavones such as for example genistein, Ginko biloba, forskolin, retinol and other retinoids, phloridzin, samphire can also be used in association.

The anti-hair loss agents and/or tonics for the hair and the nails are advantageously phytosterols, isoflavones such as for example soya isoflavones, RTH16®, Aminexil®, Minoxidil®, retinol, zinc and derivatives thereof, neoruscine, vitamin E, vitamin B2, vitamin B3, vitamin B6, vitamin PP, vitamin B5 (panthenol, bepanthen), vitamin B8 (vitamin H or biotin), vitamin B9 (folic acid), alpha hydroxyacid, quinine, certain amino acids such as cysteine, cystine, methionine. 5-alpha reductase inhibitors such as for example finasteride, dutasteride, *Serenoa serrulata* or *repens*, the extract of *Cucurbita pepo* or instead certain phytosterols, may also be used in association. Keratin, trace elements, or mineral salts can also be used in association. Certain protein or lipid plant extracts such as for example the extracts of pfaffia, sage, lemon, ginseng, quinquina, jojoba, horse chestnut, honey, wheat, nettle, echinea, coconut can also be used in association.

Anti-dandruff agents (scalp) are advantageously extract of capucin, vitamin F, thymol, clay, zinc pyrithione, zinc-PCA, zinc gluconate, zinc sulphate, camphor, extract of myrtle, salicyclic acid, vitamin B5, climbazole, ichtyol, selenium and derivatives thereof, extract of Curbicia, extract of Carthame, extract of oil of Melaleuca, oil of Bourrache and *Mimosa Tenuiflora*, Propolis, Kertyol, glycolic acid, keluamid, cyclopiroxolamine, piroctone olamine, capryloyl glycine, 5 alpha Avocuta.

The medicines or cosmetic agents that can be used in association are advantageously medicines or cosmetic agents suited for an administration by topical or oral route, in particular for the prevention and/or the treatment of atopy/eczema (corticosteroids such as hydrocortisone, desonide, fluocinolone acetonide, fluticasone propionate, topical immunomodulators, calcineurine inhibitors such as tacrolimus and pimecrolimus, cyclosporine, azathioprine, methotrexate, vitamin B12, antimicrobial molecules, anti-histamines such as hydroxyzine and diphenhydramine, antibiotics, pre- and pro-biotics, naltrexone, alpha PPAR agonists such as oleodistillate of sunflower, emollients containing ceramides or other key epidermal lipids), acne (antibiotics, benzoyl peroxide, retinoids, azelaic acid, vitamin PP, vitamin B3, zinc, cyclines), rosacea (permethol, genistein, esculoside, dextran sulphate, hesperidine methylchalcone, retinoids, licochalcone, oxymetazoline, kinetine, extract of liquorice, polyphenols, flavonoids, procyanidols (green tea, etc.), vitamin P like, extract of butcher's broom, *Sophora japonica*, extract of *Hamamelis*, antibiotics such as doxycycline) or psoriasis (corticoids, calcipotriol, calcitriol, tazarotene, cade oil, acitretine, PUVA therapy).

The immunomodulators that can be used in association are advantageously tacrolimus, pimecrolimus and oxazolines. The oxazolines that can be used in association are advantageously oxazolines selected from the group constituted of 2-undecyl-4-hydroxymethyl-4-methyl-1,3-oxazoline, 2-undecyl-4,4-dimethyl-1,3-oxazoline, (E)-4,4-dimethyl-2-heptadec-8-enyl-1,3-oxazoline, 4-hydroxymethyl-4-methyl-2-heptadecyl-1,3-oxazoline, (E)-4-hydroxymethyl-4-methyl-2-heptadec-8-enyl-1,3-oxazoline, 2-undecyl-4-ethyl-4-hydroxymethyl-1,3-oxazoline. In an even more advantageous manner, said oxazoline is 2-undecyl-4,4-dimethyl-1,3-oxazoline, called OX-100 or Cycloceramide®.

Hypopigmenting or depigmenting agents that can be used in association are hydroquinone and derivatives thereof, arbutin, retinoic acid, retinol, retinaldehyde, tretinoin, hydroquinone, corticoids, kojic acid, azelaic acid, ellagic acid, pyruvic acid, glycolic acid, vitamin B3 (niacinamide) or PP, vitamin C, Cycloceramide®, derivatives of resorcinol, resveratrol, extracts of liquorice or white mulberry, alpha-lipoic acid, linoleic acid, indomethacin, cation chelators such as EDTA (ethylene diamine tetra acetic acid), soya extracts such as genistein. Sepiwhite® (N-undecylenoyl-L-phenylalanine) commercialised by the Seppic company, which is a cosmetic depigmenting agent, may also be cited.

Pigmenting agents that can be used in association are for example agents that colour the skin such as dihydroxyacetone and melanins; agents that stimulate the natural pigmentation process such as psolarens having therapeutic properties in dermatology (8-methoxypsolarene, 5-methoxypsolaren, 4,5', 8-trimethylpsolarene or plant extracts of *Psorelea corylifolia* and of *Ammi majus*), carotenoids (lycopene, canthaxanthin), agents stimulating the cyclic AMP route (1. AMPc analogues, such as 8-bromo-AMPc or dibutiryl-AMPc, 2. forskolin, 3. isobutyl-methyl-xanthine or theophylline), activators of protein kinase C (diacylglycerols, in particular oleyl-acetyl-glycerol), aliphatic or cyclic diols(1,2-propandiol, 5-norbomane-2,2-dimethanol, norbomane-2,2-dimethano), bicyclic monoterpene diols, derivatives of tyrosine (L-tyrosine, L-DOPA), dimethylsulphoxide, lysomotropic agents, thymidine dinucleotides, fragments of DNA, analogues of the hormone stimulating the melanocytes, 3-isobutyl-1-methylxanthine, nitric acid donors (Brown, Journal of photochemistry and photobiology B: biology 63 (2001) 148-161); or instead plant extracts such as peptides of rice, and seaweeds, demonstrating a promelanogenic activity: *Laminaria digitata* (Thalitan® from Codif).

A particularly advantageous association according to the invention is a composition containing the peptide and oside extract of *Acacia macrostachya* seeds and plant and animal unsaponifiables, such as for example, the unsaponifiables of avocado and soya, and unsaponifiable concentrates of vegetable or animal oil, such as for example the concentrate of sunflower oil or palm oil, or instead vegetable oils containing unsaponifiables such as for example soya and rape oils, and derivatives of unsaponifiables such as avocado furanes, sterolic unsaponifiables, esters of sterols and vitamin derivatives. "Sterolic" unsaponifiables are unsaponifiables in which the sterols, methyl sterols and triterpenic alcohols content is comprised between 20 and 95% by weight, preferably 45-65% by weight, in relation to the total weight of the unsaponifiable.

A particularly advantageous association according to the invention is a composition containing *Acacia macrostachya* seed extract and sugars of avocado (see application WO 2005/115421). This composition is particularly adapted for the treatment of the repair of the cutaneous barrier and inflammation.

A particularly advantageous association according to the invention is a composition containing *Acacia macrostachya* seed extract and peptides of avocado (see international application WO2005/105123). This composition is particularly adapted for the treatment of irritation and inflammation.

Another particularly advantageous association according to the invention is a composition containing *Acacia mac-*

*rostachya* seed extract and an oil of avocado (see international applications WO2004/012496, WO2004/012752, WO2004/016106, WO2007/057439).

Another particularly advantageous association according to the invention is a composition containing *Acacia macrostachya* seed extract and Avocadofurane® (furanes of avocado, which can be obtained by the method disclosed in the international application WO 01/21605). This composition is particularly suited for the treatment of inflammation, to promote cicatrisation, and for the anti-ageing properties thereof.

Another particularly advantageous association according to the invention is a composition containing *Acacia macrostachya* seed extract and 5-alpha Avocuta® (butyl avocadate). This composition is particularly suited for inhibiting 5-alpha reductase (see WO 01/52837 and WO 02/06205) and regulating the seborrhoea secretion, which is increased in acne or dandruff.

Another particularly advantageous association according to the invention is a composition containing *Acacia macrostachya* seed extract and the unsaponifiables of avocado and soya. The unsaponifiables of avocado and soya that can be used in association are advantageously a mixture of furanic avocado unsaponifiables and soya unsaponifiables, in a respective ratio of around 1/3-2/3. The unsaponifiables of avocado and soya are even more advantageously the product Piascledine®, commercialised by Laboratoires Expanscience.

Another particularly advantageous association according to the invention is a composition containing *Acacia macrostachya* seed extract and an oleodistillate of sunflower, even more advantageously with linoleic concentrates of sunflower, such as the active ingredient commercialised by the Laboratoires Expanscience, Saline® (cf. the international application WO 01/21150). This composition is particularly suited for the treatment of inflammation and for the repair of the cutaneous barrier. Another particularly advantageous association according to the invention is a composition containing *Acacia macrostachya* seed extract and a soya unsaponifiable, as obtained according to the method disclosed in the international application WO01/51596.

Another particularly advantageous association according to the invention is a composition containing *Acacia macrostachya* seed extract and Lupeol (FR 2 822 821, FR 2 857 596). This composition is particularly suited for promoting cicatrisation.

Another particularly advantageous association according to the invention is a composition containing *Acacia macrostachya* seed extract and Lupin peptides as obtained according to the method disclosed in the application WO2005/102259. This composition is particularly suited for the treatment of inflammation and is used for its anti-ageing properties.

Another particularly advantageous association according to the invention is a composition containing *Acacia macrostachya* seed extract and a total extract of Lupin (see international application WO2005/102259). This composition is particularly suited for the treatment of irritations.

Another particularly advantageous association according to the invention is a composition containing *Acacia macrostachya* seed extract and an oil of Lupin, advantageously a mild white Lupin oil, as disclosed in the international application WO 98/47479.

Another particularly advantageous association according to the invention is a composition containing *Acacia macrostachya* seed extract and a peptide extract of Maca (see international application WO2004/112742). This composition is particularly appreciated for its cicatrising and anti-ageing properties.

A particularly advantageous association according to the invention is a composition containing the peptide and oside extract of *Acacia macrostachya* seeds and rice peptides (see international application WO 2008/009709). This composition is particularly appreciated for its properties of stimulating melanogenesis and the transfer of melanin.

Another particularly advantageous association according to the invention is a composition containing *Acacia macrostachya* seed extract and Cycloceramide® (derivative of oxazoline) as disclosed in the international applications WO2004050052, WO2004050079, and WO2004112741. This composition is particularly suited for the treatment of inflammatory reactions.

Another particularly advantageous association according to the invention is a composition containing *Acacia macrostachya* seed extract and an extract of Quinoa, in particular a peptide extract (see international application WO2008/080974). This composition is particularly suited for the treatment of inflammatory conditions and the repair of the cutaneous barrier.

Another particularly advantageous association according to the invention is a composition containing *Acacia macrostachya* seed extract and Cupuaçu butter. This composition is particularly appreciated for its moisturising properties.

Another particularly advantageous association according to the invention is a composition containing *Acacia macrostachya* seed extract and a concentrate of rape.

Another advantageous association according to the invention is a composition containing the extract of seeds of *Acacia macrostachya* and a corn concentrate.

Another advantageous association according to the invention is a composition containing *Acacia macrostachya* seed extract and an extract of fruit of *Schizandra sphenanthera* (see French applications FR 0955343 and FR 0955344).

Another advantageous association according to the invention is a composition containing *Acacia macrostachya* seed extract and a *Vigna unguiculata* seed extract.

All of these associations comprise at least one other active compound, in addition to the *Acacia macrostachya* seed extract, and may comprise two, three, four or more active compounds as indicated previously.

The composition according to the invention may be formulated in the form of different preparations adapted to a topical, oral, rectal, vaginal, nasal, auricular or bronchial administration, as well as a parenteral administration.

According to a first variant, the different preparations are adapted to a topical administration and include especially creams, emulsions, milks, ointments, lotions, oils, aqueous or hydro-alcoholic or glycolic solutions, powders, patches, sprays, shampoos, varnishes or any other product for external application.

According to a second variant, the different preparations are adapted to an oral administration; the *Acacia macrostachya* seed extract which can enter either a food complement or a nutraceutical composition. The food complement may be in the form of the *Acacia macrostachya* seed extract as such or instead in the form of capsules or soft capsules of gelatine or plants within the scope of the present invention. Said food complement may then contain from 10 to 100% by weight of the *Acacia macrostachya* seed extract.

The modes of administration, the posologies and the optimal galenic forms of the compounds and compositions according to the invention may be determined according to the criteria generally taken into account in the establishment of a pharmaceutical treatment, in particular dermatological, cosmetic or veterinary treatment adapted to a patient or to an animal, such as for example the age or the body weight of the patient or the animal, the seriousness of his general condition, the tolerance to the treatment, the secondary effects observed, the type of skin. As a function of the desired administration type, the composition and/or the active compounds according to the invention may moreover comprise at least one pharmaceutically acceptable excipient, especially dermatologically acceptable excipient or a cosmetically acceptable excipient. According to the first variant, an excipient suited for an administration by external topical route is used. The composition according to the present invention may moreover comprise at least one pharmaceutical or cosmetic adjuvant known to those skilled in the art, selected from thickeners, preservatives, fragrances, colorants, chemical or mineral filters, moisturising agents, thermal waters, etc.

The composition containing a *Acacia macrostachya* seed extract having the specifications indicated is particularly intended for cosmetic, pharmaceutical, dermatological or nutraceutical use.

Within the scope of a cosmetic, pharmaceutical, or dermatological use, the composition will be advantageously formulated in the form of a preparation adapted to topical administration. The composition containing a peptide and oside extract is particularly intended for a cosmetic, pharmaceutical, or dermatological use.

Within the scope of a use with a nutraceutical or cosmetic view ("cosmet-food"), the composition will be advantageously formulated in the form of a preparation adapted to an oral administration.

The invention also relates to the use of an extract of seeds of *Acacia macrostachya* for the manufacture of a cosmetic, pharmaceutical, dermatological composition or a nutraceutical composition.

Advantageously, the composition or the extract according to the present invention is used in the prevention and/or the treatment of disorders or diseases affecting the skin and/or the mucosae and/or the appendages. In a particularly advantageous manner, the extract or the composition according to the invention is used in cosmetic applications, advantageously by topical route, especially for the care or hygiene of the skin and/or the mucosae and/or the appendages such as hair, or instead for the prevention and/or the treatment of disorders of the skin and/or the mucosae and/or the appendages such as hair.

The composition or the extract according to the present invention may also be advantageously used in the prevention and/or the treatment of vascular disorders.

The composition or the extract according to the present invention may also be advantageously used in the prevention and/or the treatment of alterations of the adipose tissue.

In particular, the composition or the extract according to the invention is intended for the prevention and/or the treatment of reactions or allergic, inflammatory, irritative diseases or disorders of the skin barrier or homeostasis, of the appendages (hair and nails) and/or of the immature, normal or mature)/aged mucosae (gums, periodontium, genital mucosae).

Advantageously, the composition or the extract according to the invention may be used for the prevention and/or the treatment of reactions, disorders or diseases:
  of the skin, such as acne, rosacea or erythrocouperose, psoriasis, vascular disorders, napkin dermatitis, atopic dermatitis, eczema, contact dermatitis, irritative dermatitis, allergic dermatitis, seborrheic dermatitis (milk crust), psoriasis, sensitive skin, reactive skin, dry skin (xerosis), dehydrated skin, skin with red blotches, skin erythema, aged or photoaged skin, photosensitized skin, pigmented skin (melasma, post-inflammatory pigmentation, etc.), depigmented skin (vitiligo), skin with cellulite, loose skin, skin with stretch marks, scurf patches, chapping, stings, crevasses in particular of the breasts, sun strokes, inflammations due to rays of all types, irritations by chemical, physical agents (for example tensile load for pregnant women), bacteriological, fungicidal or viral, parasitic (lice, scabies, tinea, acarians, dermatophytosis), radiological or by innate (antimicrobial peptides) or acquired (cellular, humoral, cytokines) immuno-deficiency, and/or the mucosae such as the gums and periodontium which could exhibit gingivitis (sensitive gums of newborn infants, problems of hygiene, due to tobacco dependency or others), periodontal diseases, or genital mucosae which can exhibit irritations of the internal or external male or female genital spheres and/or appendages such as nails (brittle, fragile nails, etc.) and immature, normal or mature hair (alopacia, dandruff, hirsutism, seborrheic dermatitis, folliculitis) exhibiting in particular disorders of the scalp such as androgenetic, acute, localised, cicatricial, congenital alopecias (or pelada), occipital infants, aerata, due to chemotherapy/radiotherapy or instead effluvium telogen, anagen effluvium, pilary dystrophy, trichotillomania, tinea or greasy or dry dandruff.

The invention also relates to a method for cosmetic care of the skin and/or the appendages and/or the mucosae, in order to improve the condition and/or the appearance thereof, containing the administration or consisting in administering a composition or an extract according to the present invention.

In a particularly advantageous manner, the present invention relates to the cosmetic use of the composition or the extract to restore disorders or problems of the cutaneous barrier, to reinforce the barrier function of the skin, especially to combat against stress or environmental aggressions or chemical aggressions or irritations caused for example by medicines, on the skin, the mucosae or the appendages, especially the hair.

In particular, the composition or the extract is used advantageously in cosmetic applications for moisturising the skin or the mucosae, for treating dry skins, atopic skins, aggressed skins, sensitive skins, reactive skins, photo-sensitised skins, skins having undergone an anti-acne treatment, aged or photo-aged skins, generally speaking as anti-ageing agents of the skin (intrinsic or extrinsic ageing), especially as photo-ageing agents or anti-UV agents, for cicatrising the skin, such as anti-oxidant and anti-microbial agents, or instead for the care of hair, nails or mucosae.

EXAMPLES

Example 1

Compositions for Application by Topical Route

Several compositions for application by topical route are presented below. The peptide and oside extract of *Acacia macrostachya* may be incorporated in various cosmetic products, such as cleansing waters, oil in water emulsions, water in oil emulsions, oils, milks, lotions, shampoos, foaming products and sprays, the compositions of which are presented below by way of examples.

| MOISTURISING CLEANSING WATER | |
| --- | --- |
| Raw material/Trade name or INCI name | % |
| PURIFIED WATER | QS for 100% |
| BIOSACCHARIDE GUM | From 1 to 5% |
| BUTYLENE GLYCOL | From 1 to 5% |
| HYALURONIC ACID | From 0 to 5% |
| PEPTIDE AND OSIDE EXTRACT OF *ACACIA MACROSTACHYA* | From 0.001 to 10% |
| PRESERVATIVES | From 0 to 1% |
| CITRIC ACID MONOHYDRATE | From 0 to 1% |
| TROMETHAMINE | From 0 to 1% |

| SENSITIVE SKIN CLEANSING WATER | |
| --- | --- |
| Raw material/Trade name or INCI name | % |
| GLYCINE CAPRYLOYL | From 0 to 1% |
| SODA DETERGENT | From 0 to 1% |
| SEQUESTRANT | From 0 to 1% |
| BUTYLENE GLYCOL | From 1 to 5% |
| BETA CAROTENE | From 0 to 2% |
| *ACACIA MACROSTACHYA* EXTRACT | From 0.001 to 10% |
| PRESERVATIVES | From 0 to 1% |
| PEG 32 | From 1 to 5% |
| PEG-7 PALM COCOATE | From 1 to 5% |
| ZINC GLUCONATE | From 0 to 1% |
| CITRIC ACID | From 0 to 1% |
| PURIFIED WATER | QS for 100% |
| FRAGRANCE | From 0 to 1% |
| POLOXAMER 184 | From 1 to 5% |

| ANTI AGEING EMULSION | |
| --- | --- |
| Raw material/Trade name or INCI name | % |
| LIQUID ISOPARAFFIN | From 5 to 20% |
| ISOCETYL STEARATE | From 5 to 20% |
| HYDROXYSTEARATE AL-MG | From 5 to 20% |
| ABIL WE 09 | From 1 to 5% |
| GLYCEROL | From 1 to 5% |
| VASELINE OIL | From 1 to 5% |
| MICRONISED ZINC OXIDE | From 1 to 5% |
| BUTYLENE GLYCOL | From 1 to 5% |
| RETINOL | From 0 to 1% |
| VITAMIN C | From 0 to 5% |
| *ACACIA MACROSTACHYA* EXTRACT | From 0.01 to 10% |
| ISONONYL ISONONANOATE | From 1 to 5% |
| BEES WAX | From 1 to 5% |
| SODIUM TARTRATE | From 1 to 5% |
| SODIUM CHLORIDE | From 0 to 5% |
| GLYCINE | From 1 to 5% |
| PRESERVATIVES | From 0 to 1% |
| CHOLESTEROL | From 0 to 1% |
| PHYTOSPHINGOSINE | From 0 to 1% |
| TARTARIC ACID | From 0 to 1% |
| PURIFIED WATER | QS for 100% |

| RESTRUCTURING EMULSION | |
| --- | --- |
| Raw material/Trade name or INCI name | % |
| HYDROGENATED POLYDECENE | From 5 to 20% |
| LAURYL GLUCOSIDE CYLSTEARATE | From 1 to 5% |
| DICAPRYLYL CARBONATE | From 1 to 5% |
| GLYCEROL | From 5 to 20% |
| CARBOPOL | From 0 to 1% |
| XANTHAN GUM | From 0 to 1% |
| ASIATIC ACID | From 0 to 1% |
| VITAMIN B5 | From 0 to 5% |
| *ACACIA MACROSTACHYA* EXTRACT | From 0.01 to 10% |
| SODA DETERGENT | From 0 to 1% |
| PRESERVATIVES | From 0 to 1% |
| CITRIC ACID | From 0 to 1% |
| PURIFIED WATER | QS for 100% |

| MILK FOR DRY SKIN, ATOPICAL | |
| --- | --- |
| Raw material/Trade name or INCI name | % |
| MILD ALMOND OIL | From 1 to 5% |
| CORN OIL | From 1 to 5% |
| STEARIC ACID | From 1 to 5% |
| CETYL ALCOHOL C16 C18 | From 0 to 1% |
| ANTIFOAMING AGENT 70414 | From 0 to 1% |
| LAURIC ALCOHOL 11OE | From 1 to 5% |
| MONOLAURATE PEG 300 | From 0 to 1% |
| GLYCEROL MONOLEATE | From 0 to 1% |
| GLYCEROL MONOSTEARATE | From 1 to 5% |
| VITAMIN B12 | From 0 to 5% |
| *ACACIA MACROSTACHYA* EXTRACT | From 0.1 to 10% |
| PRESERVATIVES | From 0 to 1% |
| CITRIC ACID | From 0 to 1% |
| TRISODIUM CITRATE | From 0 to 1% |
| PURIFIED WATER | QS for 100% |
| FRAGRANCE | From 0 to 1% |
| PEANUT OIL | From 1 to 5% |
| HYDROGENATED PALM OIL | From 1 to 5% |

| ROLL-ON ANTI-BACTERIAL STICK | |
| --- | --- |
| Raw material/Trade name or INCI name | % |
| PURIFIED WATER | QS for 100% |
| BUTYLENE GLYCOL | From 1 to 5% |
| BENZOYL PEROXIDE | From 0 to 2% |
| GLYCINE CAPRILOYL | From 0 to 5% |
| ZINC PCA | From 0 to 5% |
| *ACACIA MACROSTACHYA* EXTRACT | From 0.1 to 10% |
| CARBOMER | From 0 to 2% |
| PRESERVATIVES | From 0 to 1% |
| CITRIC ACID | From 0 to 1% |
| TROMETHAMINE | From 0 to 1% |

| KERATINISING FLUID | |
| --- | --- |
| Raw material/Trade name or INCI name | % |
| CETYL ALCOHOL | From 1 to 5% |
| SILICONE 345 | From 1 to 5% |
| ANTI-OXIDANT | From 0 to 1% |
| PURIFIED WATER | QS for 100% |
| CETRIMONIUM CHLORIDE | From 0 to 5% |
| QUININE | From 0 to 5% |
| VITAMIN B5 | From 0 to 5% |
| ACACIA MACROSTACHYA EXTRACT | From 0.01 to 10% |
| HYDROLYSED WHEAT PROTEIN | From 0 to 1% |
| PRESERVATIVE | From 0 to 2% |
| FRAGRANCE | From 0 to 1% |
| pH ADJUSTER | From 0 to 1% |

| FORTIFYING HAIR LOTION | |
| --- | --- |
| Raw material/Trade name or INCI name | % |
| PURIFIED WATER | QS for 100% |
| METHYL PROPANEDIOL | From 0 to 5% |
| PRESERVATIVE | From 0 to 5% |
| pH ADJUSTER | From 0 to 5% |
| FRAGRANCE | From 0 to 1% |
| BIOTIN | From 0 to 5% |
| VITAMIN B9 | From 0 to 5% |
| ACACIA MACROSTACHYA EXTRACT | From 0.01 to 10% |
| BETA SITOSTEROL | From 0 to 1% |
| ETHYLHEXYL COCOATE | From 0 to 5% |
| PEG 40 CASTOR OIL | From 0 to 5% |

| SPF 50+ SOLAR CREAM | |
| --- | --- |
| Raw material/Trade name or INCI name | % |
| PURIFIED WATER B4 | QS for 100% |
| TITANIUM OXIDE | From 10 to 20% |
| CYCLOPENTASILOXANE | From 5 to 15% |
| OCTYL PALMITATE | From 5 to 15% |
| C12-C15 ALKYL BENZOATE | From 5 to 10% |
| DECYL PENTANOATE | From 5 to 10% |
| ZINC OXIDE | From 5 to 10% |
| GLYCEROL | From 1 to 5% |
| PEG-45/DODECYL GLYCOL COPOLYMER | From 1 to 5% |
| MACROSTACHYA ACACIA EXTRACT | From 0.01 to 10% |
| SODIUM CHLORIDE | From 1 to 5% |
| DEXTRIN PALMITATE | From 1 to 2% |
| VITAMIN E | From 0 to 2% |
| PRESERVATIVES | From 0 to 2% |
| HYDROXYPROPYL GUAR | From 0 to 1% |
| ALOE VERA | From 0 to 1% |
| SOD DETERGENT | From 0 to 1% |
| 2Na EDTA | From 0 to 1% |
| ZINC GLUTONATE | From 0 to 1% |

| VARNISH FOR FRAGILE AND BRITTLE NAILS | |
| --- | --- |
| Raw material/Trade name or INCI name | % |
| ACRYLATE COPOLYMER | From 15 to 30% |
| ETHANOL | QS for 100% |
| ACETONE | From 5 to 20% |
| MACROSTACHYA ACACIA EXTRACT | From 0.01 to 5% |

Example 2

Compositions for Administration by Oral Route

The *Acacia macrostachya* extracts may be advantageously integrated in oral compositions, typically in compositions enabling the administration of 50 mg to 200 mg of *Acacia macrostachya* extract a day.

| 1/Anti-stretch mark composition in the form of soft capsules | |
| --- | --- |
| ACACIA MACROSTACHYA EXTRACT | 30 mg |
| Awara oil | 60 mg |
| Rape oil rich in unsaponifiables | 300 mg |
| B group vitamin (B1, B2, B3, B5, B6, B9, B12) | QS for 100% of the Recommended Daily Allowance (RDA) |
| Tocotrienols | QS for 50% of the RDA |
| Vitamin E | |
| Bees wax | |
| Soya lecithin | |
| Food grade gelatine | |
| Glycerine | QS for 1 soft capsule |

This composition is administered from 4 to 6 capsules of 500 mg a day.

| 2/Anti-hair loss tablets | |
| --- | --- |
| ACACIA MACROSTACHYA EXTRACT | 25 mg |
| Extracts of cereals (wheat, buckwheat, millet, spelt wheat) rich in sulphur amino acids | 200 mg |
| Vitamin C | QS for 50% of the RDA |
| Glycosaminoglycans from fish cartilages | 200 mg |
| Glucidex IT 19 (compression agent) | QS 1 800 mg table |

This composition is administered from 5 to 8 tables a day.

| 3/Examples of slimming powder stick | |
| --- | --- |
| ACACIA MACROSTACHYA EXTRACT | 100 mg |
| Extract of tea rich in polyphenols | 100 mg |
| Extract of grapes rich in OPC | 50 mg |
| Betaglucanes of plant origin | 100 mg |

-continued

| 3/Examples of slimming powder stick | |
|---|---|
| Xanthan gum | 1 mg |
| Sodium ascorbate | 0.3 mg |
| Maltodextrin | QS for 5 g. |

This composition is administered twice a day.

| 4/Examples of anti-ageing powder stick | |
|---|---|
| ACACIA MACROSTACHYA EXTRACT | 100 mg |
| Centella asiatica extract | 100 mg |
| Magnesium, selenium, manganese | QS for 100% of RDA. |
| Xanthan gum | 1 mg |
| Sodium ascorbate | 0.3 mg |
| Maltodextrin | QS for 5 g. |

This composition is administered twice a day.

Example 3

Biological Activity Tests of the Extract According to the Invention

The peptide and oside extract of Acacia macrostachya, which is an extract prepared by hydrolysis such as enzymatic hydrolysis, is named hereafter in this example Acacia hydrolysate.

I—Preliminary Screening of Activity on Reconstructed Epidermis

The biological activities of the Acacia hydrolysate were evaluated by a test of the modulation of expression of genes on reconstructed epidermis. Thus, the expression of 64 genes of major interest in skin and cosmetic physiology was studied by PCR array on reconstructed epidermis during differentiation.

a. Materials and Methods:

The Acacia hydrolysate (0.05% and 0.1%, w/v) was added to a culture medium of reconstructed epidermis on J5. These were then incubated for 48 hours. The expression of the selected markers was evaluated by RT-PCR quantitative (PCR array).

The variation in expression of the studied markers with respect to the control was expressed in percentage (Control: 100%).

b. Results:

The most significant results are presented in the table below and tend to show that the Acacia hydrolysate, by making the gene expression of certain markers vary, has a particular interest especially in the following activities:

Cicatrisation: ↗ CLSP, cathelicidin, S100A7, Heme oxygenase 1, MMP9.

The hydration and the barrier function: ↗ Claudin 1, Desmoglein 1, Glucocerebrosidase, Loricrin, Small proline-rich proteins, Transglutaminase 1.

Anti-microbial and anti-oxidant defences: ↗ Heme oxygenase 1, Hsp27, hBD2, RNase 7, Cathelicidin.

Hair: ↗ keratin 6.

Variations in the Expression of Genes of Interest in Reconstructed Epidermis.

| | Acacia hydrolysate 0.05% | Acacia hydrolysate 0.1% |
|---|---|---|
| | % Control | |
| Calmodulin-like 5 (CLSP) | 126 | 134 |
| Cathelicidin antimicrobial peptide | 125 | 205 |
| Claudin 1 | 88 | 133 |
| Collagen, type IV, alpha 1 | 118 | 133 |
| Catenin (cadherin-associated protein), alpha 1. 102 kDa | 116 | 132 |
| Defensin, beta 4 (hBD2) | 117 | 231 |
| Desmoglein 1 | 120 | 136 |
| Glucosidase, beta; acid (includes glucocerebrosidase) | 130 | 199 |
| Heparin-binding EGF-like growth factor | 103 | 188 |
| Heme oxygenase (decycling) 1 | 167 | 280 |
| Heat shock 27 kDa protein 1 | 94 | 186 |
| Integrin, alpha 2 (CD49B, alpha 2 subunit of VLA-2 receptor) | 88 | 135 |
| Keratin 6A NM_005554 | 94 | 168 |
| Laminin, gamma 2 | 138 | 213 |
| Loricrin | 105 | 129 |
| Matrix metallopeptidase 9 (gelatinase B, 92 kDa gelatinase, 92 kDa type IV collagenase) | 134 | 278 |
| Ribonuclease, RNase A family, 7 | 186 | 379 |
| S100 calcium binding protein A7 | 126 | 242 |
| Small proline-rich protein 1B (cornifin) | 139 | 119 |
| Small proline-rich protein 2A | 170 | 669 |
| Transglutaminase 1 (K polypeptide epidermal type I, protein-glutamine-gamma-glutamyltransferase) | 114 | 136 |
| UDP-glucose ceramide glucosyltransferase | 114 | 136 |

Captions:

| Increase >+20% | Increase >+100% |
|---|---| c. Conclusions:

Thus, at the end of this screening, the activity of the Acacia hydrolysate was evaluated in two areas of interest in dermocosmetics: barrier and epidermal moisturising, as well as the dermal matrix and oxidative stress.

II. Barrier and Moisturising Function

A. Introduction

The implementation of the barrier function is linked to epidermal differentiation that results in the formation of the stratum corneum (SC). Different structures enable the SC to ensure its barrier function: the intercellular lipids, the cornified envelope, corneodesmosomes.

This barrier is reinforced by a second line of defence situated in the stratum granulosum and constituted of tight junctions.

B. Evaluation of the Gene Expression of the Markers of the Differentiation and the Barrier a. Materials and Methods:

Normal human keratinocytes were treated for 24 or 48 hours by 0.01 or 0.05% *Acacia* hydrolysate (w/v); in parallel, keratinocyte controls were cultivated under conditions favourable to differentiation ("High Ca" calcium supplemented medium). The gene expression of the selected markers was analysed by quantitative RT-PCR in real time.

The results were analysed statistically by a one-way variance analysis (ANOVA) followed by a Dunnett test:

ns p>0.05: not significant
*0.01<p<0.05: significant
**0.001<p<0.01: very significant
***p<0.001: highly significant The level of gene expression was expressed in relative quantity (RQ) and the effect of the treatment in relation to the control cells in percentage increase.

b. Results:

The *Acacia* hydrolysate very strongly and significantly increased the gene expression of keratin 1 and keratin 10. Furthermore, the *Acacia* hydrolysate significantly increased the gene expression of filaggrin, involucrin, loricrin and transglutaminase 1 (TGase 1).

All of these proteins are involved in the formation of the cornified envelope.

The *Acacia* hydrolysate thus contributes to reinforcing the cornified envelope and thus to improving the resistance of the epidermal barrier.

In addition, filaggrin, as precursor of NMF (natural moisturizing factor) is involved in the moisturising of the epidermis. Thus, through an action on the filaggrin, *Acacia* hydrolysate contributes to improving the moisturising of the epidermis.

The *Acacia* hydrolysate significantly increased the gene expression of desmoglein 1 (Dsg 1) and desmocolline-1 (Dsc 1), constituent proteins of corneodesmosomes, this effect is thus in favour of a reinforcement of the cohesion of the *stratum corneum*.

Gene Expression of Differentiation Markers and the Barrier by Keratinocytes.

|  | Control cells | *Acacia* hydrolysate 0.01% | *Acacia* hydrolysate 0.05% | Control High Ca |
|---|---|---|---|---|
| KERATIN 1 | 1.00 | 2.29 (+129% *) | 4.43 (+343% ***) | 5.42 (+442% ***) |
| KERATIN 10 | 1.00 | 2.28 (+128% *) | 3.52 (+252% ***) | 8.95 (+795% ***) |
| FILAGGRIN | 1.00 | 1.01 (+1% ns) | 1.64 (+64% **) | 4.11 (+311% ***) |
| INVOLUCRIN | 1.00 | 1.81 (+81% ***) | 1.18 (+18% ns) | 1.16 (+16>% ns) |
| LORICRIN | 1.00 | 1.54 (+54% ns) | 3.53 (+253% **) | 0.98 (−2% ns) |
| TGase 1 | 1.00 | 1.60 (+60% *) | 1.40 (+40% ns) | 2.25 (+125% ***) |
| Dsgl | 1.00 | 1.39 (+39% ns) | 1.49 (+49% *) | 3.25 (+225% ***) |
| Dscl | 1.00 | 1.57 (+57% *) | 1.38 (+38% ns) | 2.70 (+170% ***) |

C. Evaluation of the Gene Expression of Junction Proteins.

1. Screening of Expression of Junction Protein Messengers a. Materials and Methods:

The activity of *Acacia* hydrolysate was studied by quantitative RT-PCR on the level of expression of 16 genes mainly coding for tight junction proteins as well as for the major proteins of the communicating junctions of the epidermis.

Normal human keratinocytes were treated or not (control) with 0.05% and 0.1% *Acacia* hydrolysate (w/v) or the reference (1.5 mM calcium chloride $CaCl_2$) for 24 hours. The expression of the markers was evaluated by quantitative RT-PCR (PCR array).

The variation in the expression of the markers studied compared to the control was expressed in percentage (Control: 100%).

The levels of expression are classified in the following manner:

| % Relative expression compared to the control | Classification of the effect observed |
|---|---|
| >300% | Strong stimulation |
| >200% and <300% | Clear stimulation |
| >150% and <200% | Slight stimulation, to be confirmed |
| <65% and >50% | Moderate inhibition |
| <50% and >30% | Clear inhibition |
| <30% | Strong inhibition | b. Results:

The results presented below show that *Acacia* hydrolysate had a similar effect to the positive control on the expression of junction messengers: in fact, *Acacia* hydrolysate led to a significant increase in the expression of markers of Claudin 1, Occludin and Cingulin tight junctions. An inhibition in the expression of the Gap Junction Protein β2 was also observed. The communicating junction marker Gap Junction Protein β 2 code for the protein connexin 26 which is more particularly expressed in the keratinocytes in proliferation.

Thus, *Acacia* hydrolysate, by stimulating the expression of tight junction markers and by inhibiting the expression of the communicating junction marker Gap Junction Protein β 2, exhibited a pro-differentiating effect as well as a positive effect with regard to the reinforcement of the cutaneous barrier making it possible to limit the losses in water and in solutes through the para-cellular spaces.

Expression of Junction Protein Messengers (% Control)

|  | Control | $CaCl_2$ 1.5 mM (Positive control) | *Acacia* hydrolysate 0.05% | *Acacia* hydrolysate 0.1% |
|---|---|---|---|---|
| Claudin 1 | 100 | 216 | 258 | 235 |
| Occludin | 100 | 445 | 223 | 206 |
| Cingulin | 100 | 337 | 289 | 209 |
| Gap junction protein (β2 | 100 | 43 | 68 | 48 |

2. Evaluation of the Gene Expression of Tight Junction Markers a. Materials and Methods:

Normal human keratinocytes were treated for 24 or 48 hours with 0.05% or 0.1% (w/v) *Acacia* hydrolysate; in parallel, keratinocytes controls were cultivated in conditions favourable to differentiation ("High Ca" calcium supplemented medium). The gene expression of the tight junction markers was analysed by quantitative RT-PCR in real time.

The results were analysed statistically by a one way variance analysis (ANOVA) followed by a Dunnett test:
ns p>0.05: not significant
*0.01<p<0.05: significant
**0.001<p<0.01: very significant
***p<0.001: highly significant The level of gene expression was expressed in relative quantity (RQ) and the effect of the treatment compared to the control cells in percentage increase.

b. Results:

The *Acacia* hydrolysate significantly increased the gene expression of Claudin-1 and occludin, thereby confirming the results obtained during the preceding PCR array study. Through this action, and in addition to its action on filaggrin, it thus helps in maintaining the moisturising of the epidermis while limiting water losses.

Gene Expression of Tight Junction Markers by Keratinocytes.

|  | Control cells | *Acacia* hydrolysate 0.05% | *Acacia* hydrolysate 0.1% | Control High Ca |
|---|---|---|---|---|
| CLAUDIN 1 | 1.00 | 1.86 (+86% *) | 2.26 (+126% **) | 3.22 (+222% ***) |
| OCCLUDIN | 1.00 | 1.41 (+41% ns) | 1.77 (+77% *) | 2.03 (+103% ns) |

D. Conclusions

A positive effect of the *Acacia* extract according to the present invention on the different structures involved in the implementation of the barrier function has been highlighted: in fact, the *Acacia* extract is capable of positively regulating the expression of the markers of the cornified envelope, corneodesmosomes and tight junctions. These properties enable the extract (hydrolysate) of *Acacia* to contribute to the solidity and sealing of the barrier function while at the same time participating in maintaining a good level of moisturising.

III. Dermal Matrix and Oxidative Stress

A. Introduction

Modifications of the skin with age result from modifications of the cellular functions and progressive modifications of the composition and the structure of the extra-cellular dermal matrix. In fact, the dermis undergoes a gradual loss of its thickness with a reduction of essential macromolecules, such as collagen and elastin. This diminution may be attributed to a reduction in the synthesis thereof and/or to an increase in the degradation thereof by MMP (matrix metalloproteinases) for example.

The relation between oxidative stress and ageing is today well established. In fact, there is an accumulation in the aged cells of damaged molecules leading to an alteration of cellular functions. To protect itself against this oxidative stress, the cell has different anti-oxidant defence mechanisms of which the microsomal heme-oxygenase enzyme forms part.

The effect of *Acacia* hydrolysate on the modulation of the extra-cellular matrix of the dermis and on the stimulation of the anti-oxidant defences was evaluated on a dermal fibroblasts model in which the gene expression of elastin, MMP1 and heme oxygenase 1 was studied by quantitative RT-PCR in real time.

B. Materials and Methods

Normal human fibroblasts were treated for 24h with 0.01% and 0.05% *Acacia* hydrolysate (w/v) or with the reference TGFβ1 at 5 ng/ml. The gene expression of the selected markers was analysed by quantitative RT-PCR in real time.

The results were analysed statistically by a one-way variance analysis (ANOVA) followed by a Dunnett test:
ns p>0.05: not significant
*0.01<p<0.05: significant
**0.001<p<0.01: very significant
***p<0.001: highly significant The level of gene expression was expressed in relative quantity (RQ) and the effect of the treatment in relation to the control cells in percentage increase or inhibition.

C. Results

The *Acacia* hydrolysate clearly and significantly stimulated the gene expression of the elastin and very strongly and significantly inhibited the gene expression of MMPI.

Thus, the *Acacia* hydrolysate could contribute to limiting the alterations of the dermis linked to age.

Furthermore, the *Acacia* hydrolysate significantly stimulated the gene expression of heme oxygenase 1, thereby contributing to reinforcing the anti-oxidant defence mechanisms of the cell.

Gene Expression of Markers of the Dermal Matrix and Antioxidant Defences by Fibroblasts.

|  | ELASTIN | MMP1 | HEME OXYGENASE 1 |
|---|---|---|---|
| Control cells | 1.00 | 1.00 | 1.00 |
| Control (TGFβ1) | 6.59 (+559% ***) | 0.12 (−88% ***) | not determined |
| *Acacia* hydrolysate 0.01% | 1.76 (+76% **) | 0.36 (−64% ***) | 1.22 (+22% ns) |
| *Acacia* hydrolysate 0.05% | 1.52 (+52% *) | 0.43 (−57% ***) | 2.35 (+135%) *** |

E. Conclusions

With age, the dermal extra-cellular matrix alters, contributing to the thinning of the dermis.

In addition to this physiological mechanism, other factors can contribute to accelerating the skin ageing process: thus, oxygenated free radicals, produced under the influence of UV for example, can alter the different components of the cell. To defend itself, the skin has developed a complex anti-oxidant defence system, but the accumulation of free radicals can submerge this system of defence and lead to an imbalance having a tendency to result in a pro-oxidant state, which in the long term will result in the photo-ageing of the skin.

Heme oxygenase 1 forms part of said defence system, thus by stimulating its expression, the extract (hydrolysate) of *Acacia* according to the invention contributes to reinforcing the defence and protection system of the cell vis-à-vis oxidative stress.

In addition, by activating the synthesis of elastin and by limiting the expression of MMPI, the extract (hydrolysate) of *Acacia* according to the invention contributes to protecting the cell against alterations linked to ageing, whether intrinsic or extrinsic.

The invention claimed is:

1. A composition comprising an enzymatic hydrolysate of seeds of *Acacia macrostachya* and a cosmetically, pharmaceutically, dermatologically or nutraceutically acceptable excipient, wherein the seed extract enzymatic hydrolysate is a peptide and oside extract.

2. The composition of claim 1, wherein said composition comprises a dermatologically or a cosmetically acceptable excipient.

3. The composition of claim 1, wherein the peptide and oside hydrolysate comprises 10 to 90% peptides by weight and 10 to 90% sugars by weight, the percentages being expressed in relation to the total weight of said peptide and oside hydrolysate.

4. The composition of claim 3, wherein the peptide and oside hydrolysate comprises 20 to 70% peptides by weight.

5. The composition of claim 4, wherein the peptide and oside hydrolysate comprises 30 to 65% peptides by weight.

6. The composition of claim 5, wherein the peptide and oside hydrolysate comprises 45% to 50% peptides by weight.

7. The composition of claim 3, wherein the peptide and oside hydrolysate comprises 20 to 60% sugars by weight.

8. The composition of claim 7, wherein the peptide and oside hydrolysate comprises 30 to 55% sugars by weight.

9. The composition of claim 8, wherein the peptide and oside hydrolysate comprises 45% to 50% sugars by weight.

10. The composition of claim 1, further comprising at least one other active compound in addition to the *Acacia macrostachya* seed hydrolysate.

11. The composition of claim 1, wherein said composition is a cosmetic, pharmaceutical, dermatological or nutraceutical composition.

12. The composition of claim 1, wherein said composition is a topical formulation or an oral formulation.

13. The composition of claim 1 where the enzymatic hydrolysate consists essentially of peptides of at most 15000 Daltons.

14. The composition of claim 13 wherein the enzymatic hydrolysate consists essentially of peptides of from 100 Daltons to 15000 Daltons.

15. A method for preparing a peptide and oside hydrolysate of *Acacia macrostachya* seeds comprising the following successive steps:
dispersing the ground seeds in aqueous phase;
enzymatically hydrolyzing said dispersion with a mixture of proteases and carbohydrases comprising pectinase, cellulase, arabanase, hemicellulase, or β-glucanase; and
recovering the peptide and oside hydrolysate.

16. The method of claim 15, wherein the step of dispersing is carried out at a pH between 3.0 and 9.0 and at a temperature between 20 and 90° C.

17. The method of claim 15, wherein the hydrolyzed dispersion is ultra-filtered.

18. The method of claim 17, wherein the ultra-filtering is carried out at a cut-off point between 10000 and 15000 Daltons.

19. An *Acacia macrostachya* seed hydrolysate obtained by the method of claim 15, comprising 10 to 90% peptides by weight and 10 to 90% sugars by weight.

20. The hydrolysate of claim 19, comprising 20 to 70% peptides by weight.

21. The hydrolysate of claim 20, comprising 30 to 65% peptides by weight.

22. The hydrolysate of claim 21, comprising 45 to 50% peptides by weight.

23. The hydrolysate of claim 19, comprising 20% to 60% sugars by weight.

24. The hydrolysate of claim 23, comprising 30 to 55% sugars by weight.

25. The hydrolysate of claim 24, comprising 45% to 50% sugars by weight.

26. A method of treating disorders or diseases affecting skin, the mucosae, and/or appendages comprising administering the hydrolysate of claim 19.

27. A method of treating disorders or diseases affecting skin, mucosae, and/or appendages comprising administering the composition of claim 1.

28. A method of treating vascular disorders comprising administering the hydrolysate of claim 19.

29. A method of treating vascular disorders comprising administering the composition of claim 1.

30. A method of treating alterations of adipose tissue comprising administering the hydrolysate of claim 19.

31. A method of treating alterations of adipose tissue comprising administering the composition of claim 1.

32. A method of cosmetic care of skin, appendages, and/or mucosae, in order to improve the condition and/or the appearance thereof, comprising administering the composition of claim 1.

33. A method of cosmetic care of skin, appendages, and/or mucosae, in order to improve the condition and/or the appearance thereof, comprising administering the hydrolysate of claim 19.

* * * * *